(12) United States Patent
Oliverius et al.

(10) Patent No.: US 11,433,220 B2
(45) Date of Patent: Sep. 6, 2022

(54) LAYERED HIGH DENSITY ELECTRODE MAPPING CATHETER

(71) Applicant: St. Jude Medical, Cardiology Division, Inc., St. Paul, MN (US)

(72) Inventors: Andrew Oliverius, Eagan, MN (US); Neil Hawkinson, Ramsey, MN (US); Timothy S. Marass, Minneapolis, MN (US); Wade Welter, Brooklyn Park, MN (US); Nicholas Strom, Minneapolis, MN (US); Quinn Butler, Coon Rapids, MN (US); James Marrs, Arden Hills, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1004 days.

(21) Appl. No.: 16/029,038

(22) Filed: Jul. 6, 2018

(65) Prior Publication Data
US 2019/0009052 A1 Jan. 10, 2019

Related U.S. Application Data

(60) Provisional application No. 62/529,586, filed on Jul. 7, 2017.

(51) Int. Cl.
*A61M 25/00* (2006.01)
*A61B 5/00* (2006.01)
(Continued)

(52) U.S. Cl.
CPC ........... *A61M 25/008* (2013.01); *A61B 5/287* (2021.01); *A61B 5/6858* (2013.01);
(Continued)

(58) Field of Classification Search
CPC ........... A61M 25/008; A61M 25/0043; A61M 25/0074; A61M 2025/0081; A61B 5/287;
(Continued)

(56) References Cited

U.S. PATENT DOCUMENTS

| 4,522,212 A | 6/1985 | Gelinas et al. |
| 5,044,368 A | 9/1991 | Putz |

(Continued)

FOREIGN PATENT DOCUMENTS

| AU | 2015202258 A1 | 5/2015 |
| AU | 2016204351 A1 | 1/2017 |

(Continued)

OTHER PUBLICATIONS

Rao, Chepuri R.K. and Trivedi, D.C., Chemical and electrochemical depositions of platinum group metals and their applications, Coordination Chemistry Reviews, 249, (2005) pp. 613-631.

(Continued)

*Primary Examiner* — Amber R Stiles
(74) *Attorney, Agent, or Firm* — Kilpatrick Townsend & Stockton LLP

(57) ABSTRACT

Various embodiments of the present disclosure can include flexible catheter tip. The flexible catheter tip can include an inboard understructure that defines a tip longitudinal axis, wherein the inboard understructure can be formed from a first continuous element that includes a first rectangular cross-section. An intermediate inboard covering can be disposed about the first continuous element that forms a distal portion of the inboard understructure. An outboard understructure can extend along the tip longitudinal axis, wherein the outboard understructure can be formed from a second continuous element that includes a second rectangular cross-section. An intermediate outboard covering can
(Continued)

be disposed about the second continuous element that forms a distal portion of the outboard understructure.

18 Claims, 9 Drawing Sheets

(51) Int. Cl.
*A61B 18/14* (2006.01)
*A61B 5/287* (2021.01)
*A61B 18/00* (2006.01)
*A61B 18/12* (2006.01)

(52) U.S. Cl.
CPC ..... *A61B 18/1492* (2013.01); *A61M 25/0043* (2013.01); *A61M 25/0074* (2013.01); *A61B 2018/0016* (2013.01); *A61B 2018/00267* (2013.01); *A61B 2018/00357* (2013.01); *A61B 2018/00577* (2013.01); *A61B 2018/00839* (2013.01); *A61B 2018/126* (2013.01); *A61B 2018/1253* (2013.01); *A61B 2562/028* (2013.01); *A61B 2562/0209* (2013.01); *A61B 2562/164* (2013.01); *A61M 2025/0081* (2013.01)

(58) Field of Classification Search
CPC .............. A61B 5/6858; A61B 18/1492; A61B 2018/00839; A61B 2018/0016; A61B 2018/00267; A61B 2018/00357; A61B 2018/1253; A61B 2018/126; A61B 2562/0209; A61B 2562/028; A61B 2562/164; A61B 2018/00577
See application file for complete search history.

(56) References Cited

U.S. PATENT DOCUMENTS

| | | | |
|---|---|---|---|
| 5,156,151 A | 10/1992 | Imran | |
| 5,450,846 A | 9/1995 | Galdreyer | |
| 5,465,717 A | 11/1995 | Imran et al. | |
| 5,647,870 A | 7/1997 | Kordis et al. | |
| 5,702,438 A | 12/1997 | Avitall | |
| 5,836,947 A | 11/1998 | Fleischman et al. | |
| 5,846,196 A | 12/1998 | Siekmeyer et al. | |
| 5,879,295 A | 3/1999 | Li et al. | |
| 5,893,847 A | 4/1999 | Kordis | |
| 5,904,680 A | 5/1999 | Kordis et al. | |
| 5,964,757 A | 10/1999 | Ponzi | |
| 6,029,091 A | 2/2000 | de la Rama et al. | |
| 6,071,282 A * | 6/2000 | Fleischman ........ A61B 18/1492 600/374 | |
| 6,120,476 A | 9/2000 | Fung et al. | |
| 6,123,699 A | 9/2000 | Webster, Jr. | |
| 6,171,277 B1 | 1/2001 | Ponzi | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,216,043 B1 | 4/2001 | Swanson et al. | |
| 6,267,746 B1 | 7/2001 | Bumbalough | |
| 6,415,187 B1 | 7/2002 | Kuzma et al. | |
| 6,430,426 B2 | 8/2002 | Avitall | |
| 6,454,766 B1 * | 9/2002 | Swanson ............ A61B 18/1492 606/41 | |
| 6,477,423 B1 | 11/2002 | Jenkins | |
| 6,522,932 B1 | 2/2003 | Kuzma et al. | |
| 6,652,515 B1 | 11/2003 | Maguire et al. | |
| 6,658,302 B1 | 12/2003 | Kuzma et al. | |
| 6,961,602 B2 | 11/2005 | Fuimaono et al. | |
| 7,027,851 B2 | 4/2006 | Mejia | |
| 7,089,045 B2 | 8/2006 | Fuimaono et al. | |
| 7,099,712 B2 | 8/2006 | Fuimaono et al. | |
| 7,228,164 B2 | 6/2007 | Fuimaono et al. | |
| 7,257,435 B2 | 8/2007 | Plaza | |
| 7,412,274 B2 | 8/2008 | Mejia | |
| 7,429,261 B2 | 9/2008 | Kunis et al. | |
| 7,561,907 B2 | 7/2009 | Fuimaono et al. | |
| 8,103,327 B2 | 1/2012 | Harlev et al. | |
| 8,157,848 B2 | 4/2012 | Zhang et al. | |
| 8,271,099 B1 | 9/2012 | Swanson | |
| 8,364,234 B2 | 1/2013 | Kordis et al. | |
| 8,364,236 B2 | 1/2013 | Burke et al. | |
| 8,391,947 B2 | 3/2013 | Urman et al. | |
| 8,486,063 B2 | 7/2013 | Werneth et al. | |
| 8,560,086 B2 | 10/2013 | Just et al. | |
| 8,565,894 B2 | 10/2013 | Vetter et al. | |
| 8,603,069 B2 | 12/2013 | Selkee | |
| 8,744,599 B2 | 6/2014 | Tegg | |
| 8,795,504 B2 | 8/2014 | Petrossians et al. | |
| 8,903,508 B2 | 12/2014 | Feler | |
| 9,044,245 B2 | 6/2015 | Condie et al. | |
| 9,474,894 B2 | 10/2016 | Mercanzini et al. | |
| 9,820,664 B2 | 11/2017 | Hotlink et al. | |
| 9,833,608 B2 | 12/2017 | Masson | |
| 9,907,480 B2 | 3/2018 | Basu et al. | |
| 9,949,656 B2 | 4/2018 | Wu et al. | |
| 2001/0047129 A1 | 11/2001 | Hall et al. | |
| 2002/0087208 A1 * | 7/2002 | Koblish ............ A61B 18/1492 607/113 | |
| 2003/0050636 A1 | 3/2003 | Swanson et al. | |
| 2003/0120328 A1 | 6/2003 | Jenkins et al. | |
| 2004/0186546 A1 | 9/2004 | Mandrusov et al. | |
| 2005/0004440 A1 * | 1/2005 | Vanney ............ A61B 18/1492 600/374 | |
| 2005/0159741 A1 | 7/2005 | Paul et al. | |
| 2007/0066878 A1 | 3/2007 | Worley et al. | |
| 2007/0123852 A1 | 5/2007 | Deem et al. | |
| 2007/0219546 A1 | 9/2007 | Mody et al. | |
| 2008/0140152 A1 | 6/2008 | Imran et al. | |
| 2008/0243214 A1 | 10/2008 | Koblish | |
| 2008/0312521 A1 | 12/2008 | Solomon | |
| 2008/0319418 A1 | 12/2008 | Chong | |
| 2009/0149848 A1 | 6/2009 | Werneth et al. | |
| 2009/0198300 A1 | 8/2009 | Zhang et al. | |
| 2009/0240248 A1 | 9/2009 | Deford et al. | |
| 2010/0016848 A1 | 1/2010 | Desai | |
| 2010/0076426 A1 | 3/2010 | de la Rama et al. | |
| 2010/0286684 A1 | 11/2010 | Hata et al. | |
| 2011/0106074 A1 | 5/2011 | Kunis et al. | |
| 2011/0118726 A1 | 5/2011 | de la Rama et al. | |
| 2011/0160720 A1 | 6/2011 | Johnson | |
| 2011/0160721 A1 | 6/2011 | Wang et al. | |
| 2011/0190732 A1 | 8/2011 | Majercak et al. | |
| 2011/0238054 A1 * | 9/2011 | Kim ................... A61B 18/1815 606/33 | |
| 2011/0313417 A1 | 12/2011 | de la Rama et al. | |
| 2012/0172697 A1 | 7/2012 | Urman et al. | |
| 2012/0271302 A1 | 10/2012 | Behl et al. | |
| 2012/0296232 A1 | 11/2012 | Ng | |
| 2013/0012938 A1 | 1/2013 | Asirvatham et al. | |
| 2013/0231659 A1 | 9/2013 | Hill et al. | |
| 2013/0253504 A1 | 9/2013 | Fang | |
| 2013/0274582 A1 | 10/2013 | Afonso et al. | |
| 2014/0142408 A1 | 5/2014 | de la Rama et al. | |
| 2014/0200639 A1 * | 7/2014 | De La Rama ....... A61N 1/0476 607/116 | |
| 2014/0288552 A1 | 9/2014 | Kunis et al. | |
| 2014/0296849 A1 | 10/2014 | Coe et al. | |
| 2014/0296902 A1 | 10/2014 | Huszar et al. | |
| 2014/0316496 A1 | 10/2014 | Masson et al. | |
| 2014/0336636 A1 | 11/2014 | Huszar et al. | |
| 2014/0350564 A1 | 11/2014 | Huszar et al. | |
| 2015/0105645 A1 | 4/2015 | Subramaniam et al. | |
| 2015/0133760 A1 | 5/2015 | Kordis et al. | |
| 2015/0141785 A1 | 5/2015 | Hayam et al. | |
| 2015/0159741 A1 | 6/2015 | Versteyhe et al. | |
| 2015/0351652 A1 | 12/2015 | Marecki et al. | |
| 2016/0143588 A1 * | 5/2016 | Hoitink ............. A61B 5/6859 600/374 | |
| 2016/0151113 A1 | 6/2016 | Kim et al. | |
| 2016/0213916 A1 | 7/2016 | de la Rama | |
| 2016/0317094 A1 | 11/2016 | Byrd et al. | |
| 2016/0331471 A1 | 11/2016 | Deno et al. | |

(56) References Cited

U.S. PATENT DOCUMENTS

| | | |
|---|---|---|
| 2016/0374582 A1 | 12/2016 | Wu et al. |
| 2016/0374753 A1 | 12/2016 | Wu et al. |
| 2017/0000365 A1 | 1/2017 | Wu et al. |
| 2017/0042449 A1 | 2/2017 | Deno et al. |
| 2017/0049348 A1 | 2/2017 | Deno et al. |
| 2017/0112404 A1 | 4/2017 | de la Rama et al. |
| 2017/0112405 A1 | 4/2017 | Sterrett et al. |
| 2017/0319269 A1 | 11/2017 | Oliverius et al. |
| 2017/0367756 A1 | 12/2017 | Sliwa et al. |
| 2018/0050190 A1 | 2/2018 | Masson |
| 2018/0056038 A1 | 3/2018 | Aujla |
| 2018/0070845 A1 | 3/2018 | Hoitink et al. |
| 2018/0116539 A1 | 5/2018 | Olson et al. |
| 2018/0193089 A1 | 7/2018 | Wu |
| 2018/0335519 A1 | 11/2018 | Gliner et al. |
| 2018/0374582 A1 | 12/2018 | Holmes et al. |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 101797181 A | 8/2010 |
| CN | 103908342 A | 7/2014 |
| CN | 104159536 A | 11/2014 |
| CN | 104968261 A | 10/2015 |
| CN | 105615994 A | 6/2016 |
| CN | 105960201 A | 9/2016 |
| CN | 106264715 A | 1/2017 |
| CN | 106264716 A | 1/2017 |
| CN | 106308790 A | 1/2017 |
| EP | 0779059 A1 | 6/1997 |
| EP | 2664295 A1 | 11/2013 |
| EP | 2732843 A1 | 5/2014 |
| EP | 2747680 A2 | 7/2014 |
| EP | 2752153 A1 | 7/2014 |
| EP | 2792322 A1 | 10/2014 |
| EP | 2792323 A1 | 10/2014 |
| EP | 2796103 A1 | 10/2014 |
| EP | 2907462 A1 | 8/2015 |
| EP | 3023052 A | 5/2016 |
| EP | 3111871 A1 | 1/2017 |
| EP | 3111872 A1 | 1/2017 |
| EP | 3114987 A1 | 1/2017 |
| EP | 3363397 A1 | 8/2018 |
| EP | 3527125 A1 | 8/2019 |
| IL | 246415 A | 12/2019 |
| JP | 2002-126096 A | 5/2002 |
| JP | 2009500052 A | 1/2009 |
| JP | 2010057943 A | 3/2010 |
| JP | 2012130392 A | 7/2012 |
| JP | 2017012750 A | 1/2017 |
| JP | 2017012755 A | 1/2017 |
| JP | 2017038919 A | 2/2017 |
| RU | 2016124794 A | 12/2017 |
| RU | 2016124801 A | 12/2017 |
| RU | 2016125763 A | 1/2018 |
| WO | 94/21166 A1 | 9/1994 |
| WO | 2004112629 A1 | 12/2004 |
| WO | 2005114720 A2 | 12/2005 |
| WO | 2007001981 A2 | 1/2007 |
| WO | 2008157399 A1 | 12/2008 |
| WO | 2011075328 A1 | 6/2011 |
| WO | 2012092016 A1 | 7/2012 |
| WO | 2012/145072 A1 | 10/2012 |
| WO | 2013131046 A1 | 6/2013 |
| WO | 2014113612 A1 | 7/2014 |
| WO | 2015057521 A1 | 4/2015 |
| WO | 2015095577 A1 | 6/2015 |
| WO | 2015130824 A1 | 9/2015 |
| WO | 2016001015 A1 | 1/2016 |
| WO | 2016090175 A1 | 6/2016 |

OTHER PUBLICATIONS

Sheela G., et al., Electrodeposition of Iridium, Bulletin of Electrochemistry, 15 (5-6) May-Jun. 1999, pp. 208-210.
Wu, Feng, et al., Electrodeposition of Platinum-Iridium Alloy on Nickel-Base Single-Crystal Superalloy TMS75, Surface and Coatings Technology vol. 184, Issue 1, Jun. 1, 2004.
Baumgartner, M.E. and Raub, CH. J., The Electrodeposition of Platinum and Platinum Alloys, Platinum Metals Review, 1988, 32, (4), 188-197.
Ohno, Izumi, Electroless Deposition of Palladium and Platinum, Modern Electroplating, 5th Edition, Edited by Mordechay Schlesinger and Milan Paunovic, Copyright 2010, John Wiley & Sons, Inc. Chp 20, 477-482.
Electroplating the Platinum Metals—A Recent Survey of Processes and Applications, Platinum Metals Rev., 1970, 14, (3) pp. 93-94.
Yingna Wu et al., Characterization of Electroplated Platinum-Iridium Alloys on the Nickel-Base Single Crystal Superalloy, Materials Transactions, vol. 46, No. 10 (2005) pp. 2176-2179.

\* cited by examiner

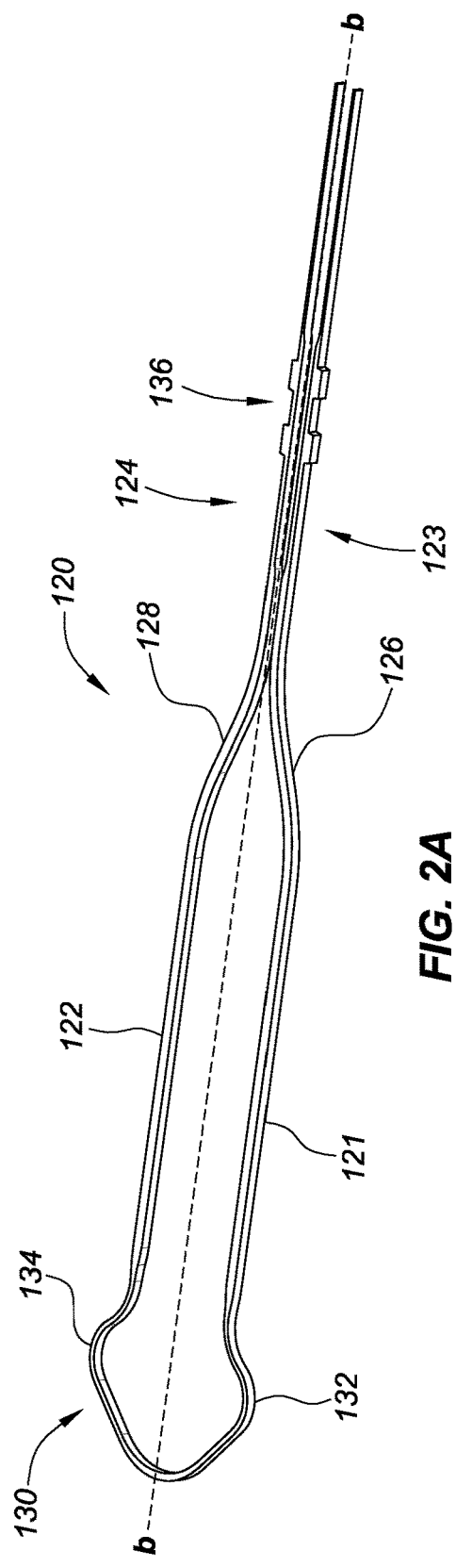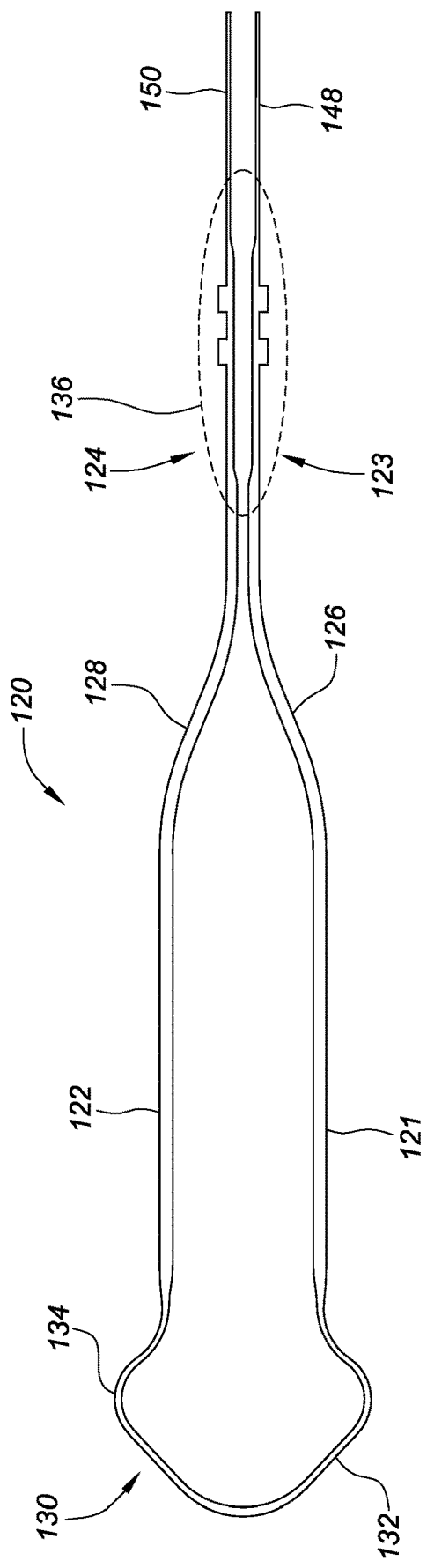

LAYERED HIGH DENSITY ELECTRODE MAPPING CATHETER

CROSS-REFERENCE TO RELATED APPLICATION

This application claims priority to U.S. application No. 62/529,586 (the '568 application) titled "LAYERED HIGH DENSITY ELECTRODE MAPPING CATHETER," filed 7 Jul. 2017. The '568 application is hereby incorporated by reference as though fully set forth herein.

a. Field of the Disclosure

This disclosure relates to a layered high density electrode mapping catheter.

b. Background Art

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter and constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring electrodes. It can be difficult to maintain good electrical contact with cardiac tissue when using these conventional catheters and their relatively rigid (or nonconforming), metallic electrodes, especially when sharp gradients and undulations are present.

Whether mapping or forming lesions in a heart, the beating of the heart, especially if erratic or irregular, complicates matters, making it difficult to keep adequate contact between electrodes and tissue for a sufficient length of time. These problems are exacerbated on contoured or trabeculated surfaces. If the contact between the electrodes and the tissue cannot be sufficiently maintained, quality lesions or accurate mapping are unlikely to result.

The foregoing discussion is intended only to illustrate the present field and should not be taken as a disavowal of claim scope.

BRIEF SUMMARY

Various embodiments of the present disclosure can include flexible catheter tip. The flexible catheter tip can include an inboard understructure that defines a tip longitudinal axis, wherein the inboard understructure can be formed from a first continuous element that includes a first rectangular cross-section. An intermediate inboard covering can be disposed about the first continuous element that forms a distal portion of the inboard understructure. An outboard understructure can extend along the tip longitudinal axis, wherein the outboard understructure can be formed from a second continuous element that includes a second rectangular cross-section. An intermediate outboard covering can be disposed about the second continuous element that forms a distal portion of the outboard understructure.

Various embodiments of the present disclosure can include a flexible catheter tip. The flexible catheter tip can include a flexible understructure that defines a tip longitudinal axis, wherein the flexible understructure is formed from a first continuous element that includes a first rectangular cross-section. The flexible catheter tip can include an intermediate covering disposed about the first continuous element. The flexible catheter tip can include a covering disposed over the intermediate covering, such that the intermediate covering is disposed between the covering and the flexible understructure.

Various embodiments of the present disclosure can include a flexible catheter tip. The flexible catheter tip can include an inboard understructure that defines a tip longitudinal axis, wherein the inboard understructure is formed from a first continuous element that includes a first rectangular cross-section, the first continuous element defining first and second inboard arm understructures and a flared head portion connected to a distal end of each of the first and second inboard arm understructures. The flexible catheter tip can include an intermediate inboard covering disposed about the flared head portion. The flexible catheter tip can include an outboard understructure that extends along the tip longitudinal axis, wherein the outboard understructure is formed from a second continuous element that includes a second rectangular cross-section, the second continuous element defining first and second outboard arm understructures and a head portion connected to a distal end of each of the first and second outboard arm understructures. The flexible catheter tip can include an intermediate outboard covering disposed about the second continuous element that forms the head portion.

BRIEF DESCRIPTION OF THE DRAWINGS

FIG. 2A is an isometric side and top view of an inboard understructure of a high density electrode mapping catheter in FIG. 1A, according to various embodiments of the present disclosure.

FIG. 2B is a top view of the inboard understructure depicted in FIG. 2A, according to various embodiments of the present disclosure.

DETAILED DESCRIPTION

The contents of International Application No. PCT/US2014/011940 entitled Flexible High-Density Mapping Catheter Tips and Flexible Ablation Catheter Tips with Onboard High-Density Mapping Electrodes and U.S. application Ser. No. 15/331,369 entitled High Density Electrode Mapping Catheter are hereby incorporated by reference as though fully set forth herein.

Figure 1A:
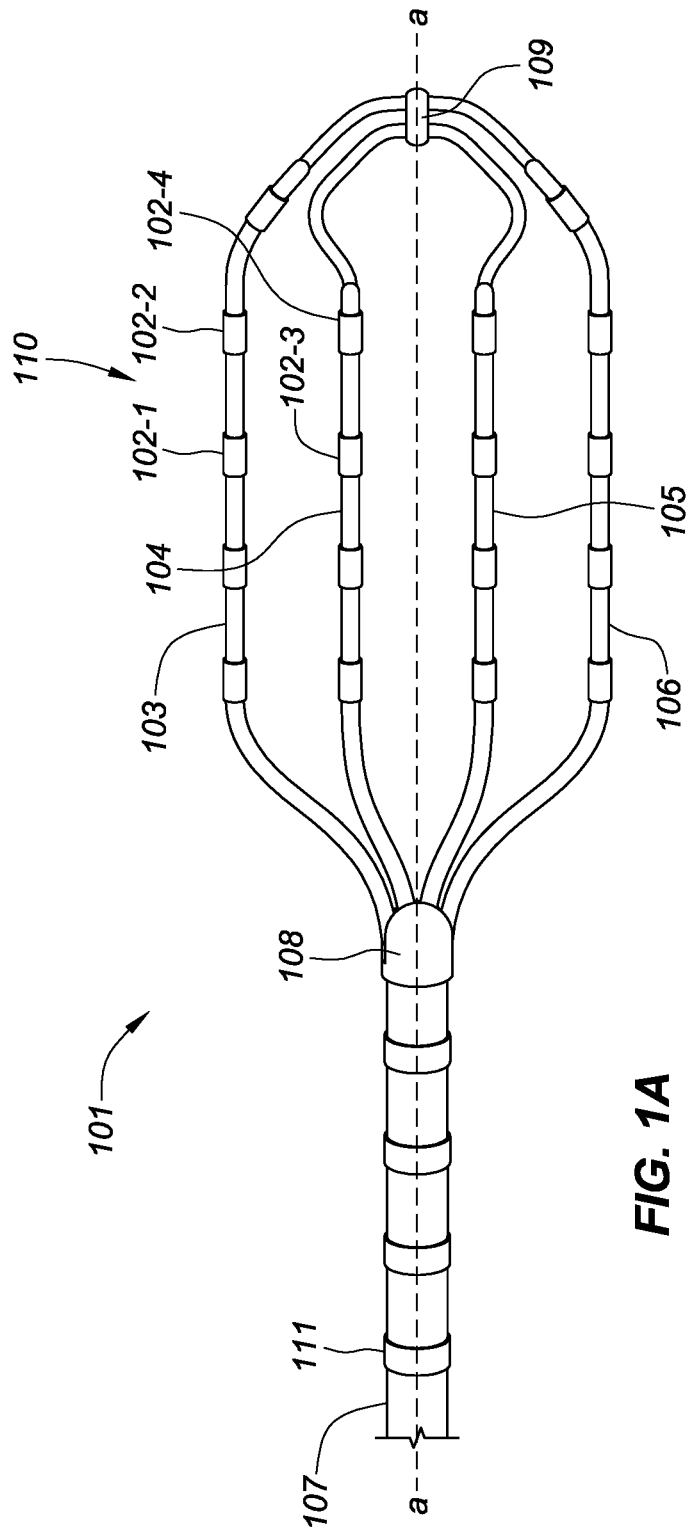
FIG. 1A is a top view of a high density electrode mapping catheter, according to various embodiments of the present disclosure.
Figure 1B:
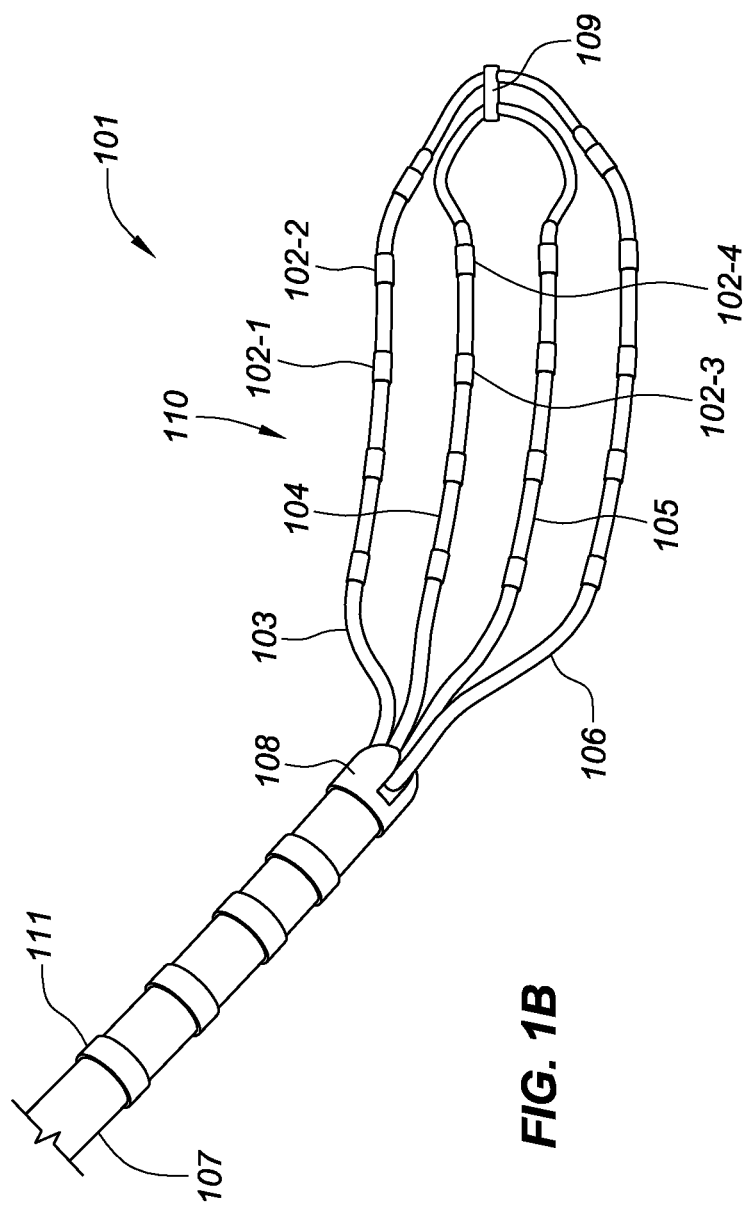
FIG. 1B is an isometric side and top view of the high density electrode mapping catheter in FIG. 1A, according to various embodiments of the present disclosure.

FIG. 1A is a top view of a high density electrode mapping catheter 101 and FIG. 1B is an isometric side and top view of the high density electrode mapping catheter 101, according to various embodiments of the present disclosure. In some embodiments, the high density electrode mapping catheter 101 can include a flexible tip portion 110 that forms a flexible array of microelectrodes 102-1, 102-2, 102-3, 102-4. Hereinafter, microelectrodes 102-1, 102-2, 102-3, 102-4 are referred to in the plural as microelectrodes 102. For ease of reference, only four microelectrodes 102 are labeled in FIG. 1A, however, the high density mapping catheter 101 can include more than four microelectrodes, as depicted. This planar array (or 'paddle' configuration) of microelectrodes 102 comprises four side-by-side, longitudinally-extending arms 103, 104, 105, 106, which can form a flexible framework on which the microelectrodes 102 are disposed. The four microelectrode-carrier arms comprise a first outboard arm 103, a second outboard arm 106, a first inboard arm 104, and a second inboard arm 105, which can be connected via a distal coupler 109. These arms can be laterally separated from each other.

Each of the four arms can carry a plurality of microelectrodes 102. For example, each of the four arms can carry microelectrodes 102 spaced along a length of each of the four arms. Although each of the high density electrode mapping catheters 101 depicted in FIGS. 1A and 1B depict four arms, the high density electrode mapping catheters 101 could comprise more or fewer arms. Additionally, while the high density electrode mapping catheter 101 depicted in FIGS. 1A and 1B is depicted as including 18 electrodes (e.g., 5 microelectrodes on first outboard arm 103 and second outboard arm 106 and 4 microelectrodes on first inboard arm 104 and second inboard arm 105) the catheters can include more or fewer than 18 electrodes. In addition, the first outboard arm 103 and second outboard arm 106 can include more or fewer than 5 microelectrodes and the first inboard arm 104 and second inboard arm 105 can include more or fewer than 4 microelectrodes).

In some embodiments, the microelectrodes 102 can be used in diagnostic, therapeutic, and/or mapping procedures. For example and without limitation, the microelectrodes 102 can be used for electrophysiological studies, pacing, cardiac mapping, and/or ablation. In some embodiments, the microelectrodes 102 can be used to perform unipolar or bipolar ablation. This unipolar or bipolar ablation can create specific lines or patterns of lesions. In some embodiments, the microelectrodes 102 can receive electrical signals from the heart, which can be used for electrophysiological studies. In some embodiments, the microelectrodes 102 can perform a location or position sensing function related to cardiac mapping.

In some embodiments, the high density electrode mapping catheter 101 can include a catheter shaft 107. The catheter shaft 107 can include a proximal end and a distal end. The distal end can include a connector 108, which can couple the distal end of the catheter shaft 107 to a proximal end of the planar array. The catheter shaft 107 can define a catheter shaft longitudinal axis aa, as depicted in FIG. 1A, along which the first outboard arm 103, first inboard arm 104, second inboard arm 105, and second outboard arm 106 can generally extend parallel in relation therewith. The catheter shaft 107 can be made of a flexible material, such that it can be threaded through a tortuous vasculature of a patient. In some embodiments, the catheter shaft 107 can include one or more ring electrodes 111 disposed along a length of the catheter shaft 107. The ring electrodes 111 can be used for diagnostic, therapeutic, and/or mapping procedures, in an example.

As depicted in FIG. 1B, the flexible tip portion 110 can be adapted to conform to tissue (e.g., cardiac tissue). For example, when the flexible tip portion 110 contacts tissue, the flexible tip portion 110 can deflect, allowing the flexible framework to conform to the tissue. In some embodiments, the arms (or the understructure of the arms) comprising the paddle structure (or multi-arm, electrode-carrying, flexible framework) at the distal end of the catheters depicted in FIGS. 1A and 1B can be laser cut from a flexible or spring-like material such as Nitinol and/or a flexible substrate, as discussed herein. In some embodiments, the arms (or the understructure of the arms) can be formed from a sheet of metal (e.g., Nitinol) with a uniform thickness. Different portions of the arms (or understructure of the arms) can be formed from the sheet (e.g., cut) such that the different portions of the arms have varying widths. The construction (including, for example, the length and/or diameter of the arms) and material of the arms can be adjusted or tailored to create, for example, desired resiliency, flexibility, foldability, conformability, and stiffness characteristics, including one or more characteristics that may vary from the proximal end of a single arm to the distal end of that arm, or between or among the plurality of arms comprising a single paddle structure. The foldability of materials such as Nitinol and/or another type of flexible substrate provide the additional advantage of facilitating insertion of the paddle structure into a delivery catheter or introducer, whether during delivery of the catheter into the body or removal of the catheter from the body at the end of a procedure.

In some embodiments, the arms can have a rectangular cross-section and can have defined edges. The arms can be housed in an atraumatic covering, which can be a thin-walled polymer (e.g., urethane) extrusion. The atraumatic covering can prevent the edges of the arms from contacting tissue, thus preventing damage to the tissue. In some embodiments, as the arms flex as a result of contact with tissue and/or from deployment from a sheath, the arms and in particular the edges of the arms can contact the atraumatic covering. Contact between the edges of the arms and the atraumatic covering can cause wear to the atraumatic covering and can eventually cause holes to be formed in the atraumatic covering. As further discussed herein, embodiments of the present disclosure can provide a solution to this potential occurrence. Additionally, embodiments, of the present disclosure can prevent a stretching/shrinking, of the atraumatic covering, which can decrease an amount of wear caused to the atraumatic covering.

Among other things, the disclosed catheters, with their plurality of microelectrodes, are useful to (1) define regional propagation maps of particularly sized areas (e.g., one centimeter square areas) within the atrial walls of the heart; (2) identify complex fractionated atrial electrograms for ablation; (3) identify localized, focal potentials between the microelectrodes for higher electrogram resolution; and/or (4) more precisely target areas for ablation. These mapping catheters and ablation catheters are constructed to conform to, and remain in contact with, cardiac tissue despite potentially erratic cardiac motion. Such enhanced stability of the catheter on a heart wall during cardiac motion provides more accurate mapping and ablation due to sustained tissue-electrode contact. Additionally, the catheters described herein may be useful for epicardial and/or endocardial use. For example, the planar array embodiments depicted herein may be used in an epicardial procedure where the planar array of microelectrodes is positioned between the myocardial surface and the pericardium. Alternatively the planar array embodiments may be used in an endocardial procedure to quickly sweep and/or analyze the inner surfaces of the myocardium and quickly create high-density maps of the heart tissue's electrical properties.

FIG. 2A is an isometric side and top view of an inboard understructure 120 (also referred to herein as inner understructure) of the high density electrode mapping catheter depicted in FIG. 1A, according to various embodiments of the present disclosure. In some embodiments, the inboard understructure 120 can be formed from a flexible or spring-like material such as Nitinol and/or a flexible substrate, as discussed herein. In an example, the inboard understructure can be cut from a planar sheet of material (e.g., planar substrate). The inboard understructure 120 can include a first inboard arm understructure 121 and a second inboard arm understructure 122. Although not shown, the outboard understructure (also referred to herein as outer understructure) that provides the understructure for the first outboard arm 103 and the second outboard arm 106 can be formed and/or processed in a manner analogous to that discussed in relation to the inboard understructure 120. Further, if the high density electrode mapping catheter includes additional arms, those arms can be formed and/or processed in a manner analogous to that discussed in relation to the inboard understructure 120. For the sake of brevity, discussion is directed towards the inboard understructure 120. As depicted, the inboard understructure 120 can include a first proximal inboard mounting arm 123 and a second proximal inboard mounting arm 124. The proximal inboard mounting arms can be inserted into a distal end of the catheter 107 and through the connector 108 and can be used to connect the flexible tip portion 110 to the distal end of the catheter 107. In some embodiments, the proximal inboard mounting arms can be inserted through a torsional spacer, as discussed herein.

In some embodiments, the inboard understructure 120 can define a tip longitudinal axis, depicted by line bb. In some embodiments, the inboard understructure 120 can be formed from a continuous element that includes a first rectangular cross-section. As used herein, a rectangular cross-section can include a square cross-section. For example, the inboard understructure 120 can include the first proximal inboard mounting arm 123 and second proximal inboard mounting arm 124, which can extend along the longitudinal axis. The inboard understructure 120 can include a first inboard arm understructure 121 that extends distally from the first proximal inboard mounting arm 123 and can include a second inboard arm understructure 122 that extends distally from the second proximal inboard mounting arm 124. In some embodiments, the first inboard arm understructure 121 and the second inboard arm understructure 122 can extend parallel to the tip longitudinal axis bb and to one another.

In some embodiments, a first transition understructure portion 126 can be disposed between the first proximal inboard mounting arm 123 and the first inboard arm understructure 121. The first transition understructure portion 126 can be laterally flared away from the tip longitudinal axis bb. Additionally, a second transition understructure portion 127 can be disposed between the second proximal inboard mounting arm 124 and the second inboard arm understructure 122. The second transition understructure portion 128 can be laterally flared away from the tip longitudinal axis bb. In an example, the first transition understructure portion 126 and the second transition understructure portion 128 can be flared away from one another.

In some embodiments, the inboard understructure 120 includes a flared head portion 130 that is connected to distal ends of the first and second inboard arm understructures 121, 122. In some embodiments, the flared head portion 130 can be formed from a first flared element 132 and a second flared element 134. As the first flared element 132 and the second flared element 134 extend distally, the elements 132, 134 can be laterally flared away from the tip longitudinal axis bb and away from one another, before extending toward the tip longitudinal axis bb and toward one another. The first flared element 132 and the second flared element 134 can be connected along the tip longitudinal axis bb. In an example, the inboard understructure can be symmetrical along either side of the tip longitudinal axis bb.

In some embodiments, the proximal portion of the inboard frame understructure 120 can include the first proximal inboard mounting arm 123 and the second proximal inboard mounting arm 124. In an example, the proximal portion of the inboard frame understructure 120 can include an inboard frame lock portion 136.

FIG. 2B depicts a top view of the inboard understructure 120 depicted in FIG. 2A, according to various embodiments of the present disclosure. FIG. 2B depicts the inboard frame lock portion 136 of the proximal inboard portion of the inboard frame understructure 120. In some embodiments, a distal end of the first proximal inboard mounting arm 123 and the second proximal inboard mounting arm 124 can be connected to a proximal end of the first transition understructure portion 126 and the second transition understructure portion 128, respectively. The first proximal inboard mounting arm 123 can have a reduced lateral width with respect to the first transition understructure portion 126 and the second proximal inboard mounting arm 124 can have a reduced lateral width with respect to the second transition understructure portion 128. In an example, the transition understructure portions 126, 128 and the proximal inboard mounting arms 123, 124 can be tapered at a tapered transition area between the two elements, as further depicted in FIG. 2C.

In some embodiments, a proximal end of the inboard frame lock portion 136 can be connected to a proximal tail portion that includes a first proximal tail 148 and a second proximal tail 150. The first proximal tail 148 can be connected to the first proximal inboard mounting arm 123 and the second proximal tail 150 can be connected to the second proximal inboard mounting arm 124.

As previously discussed, each portion of the inboard frame understructure 120 (FIG. 2A, 2B), including the proximal tails 148, 150, proximal inboard mounting arms 123, 124, inboard arm understructures 121, 122, and flared head portion 130 can be formed from a planar substrate. For example, the planar substrate can have a rectangular cross-section, which can be beneficial, as further described herein. In some approaches, high density electrode mapping catheters can be assembled using tubular subassemblies for the inboard understructure and the outboard understructure. One reason for the use of tubing when assembling the understructures is to allow wire to be threaded through the tubing for connection of each individual microelectrode. This process can be labor and/or cost intensive, since each wire may be individually threaded through the tubing and individually connected with each microelectrode. Further, ensuring that a reliable electrical connection is established between each microelectrode and its wire can be challenging.

In addition, use of tubing can result in a less predictable deflection of the flexible tip portion since the walls of the tubing may be symmetrical and are not biased to bend in a particular manner. Embodiments of the present disclosure can provide for a more predictable deflection of the flexible tip portion 110. In addition, embodiments of the present disclosure can maintain a lateral spacing between electrodes disposed on the inboard understructure and an outboard understructure, as further discussed herein. However, a byproduct of the planar substrate (e.g., having a rectangular cross-section) can include contact between the edges of the arms and an atraumatic covering that houses the planar substrate, which can cause wear to the atraumatic covering and can eventually cause holes to be formed in the atraumatic covering. Embodiments of the present disclosure can provide a solution to this potential occurrence.

As depicted in FIGS. 2A and 2B, the inboard understructure 120 (and although not depicted, the outboard understructure) can be formed from a planar piece of material. In an example, the inboard understructure 120 (and the outboard understructure) can be formed from an understructure with a rectangular and/or square shaped cross-section. In some embodiments, the inboard understructure 120 and/or the outboard understructure can be a continuous element that is formed from a single unitary piece of material. As used herein, a rectangular cross-section can be defined as a cross-section having a greater width than thickness. However, in some embodiments, a rectangular cross-section can include a cross-section having a greater thickness than width. As used herein, a square cross-section can be defined as a cross-section having a same width and thickness.

Figure 3:
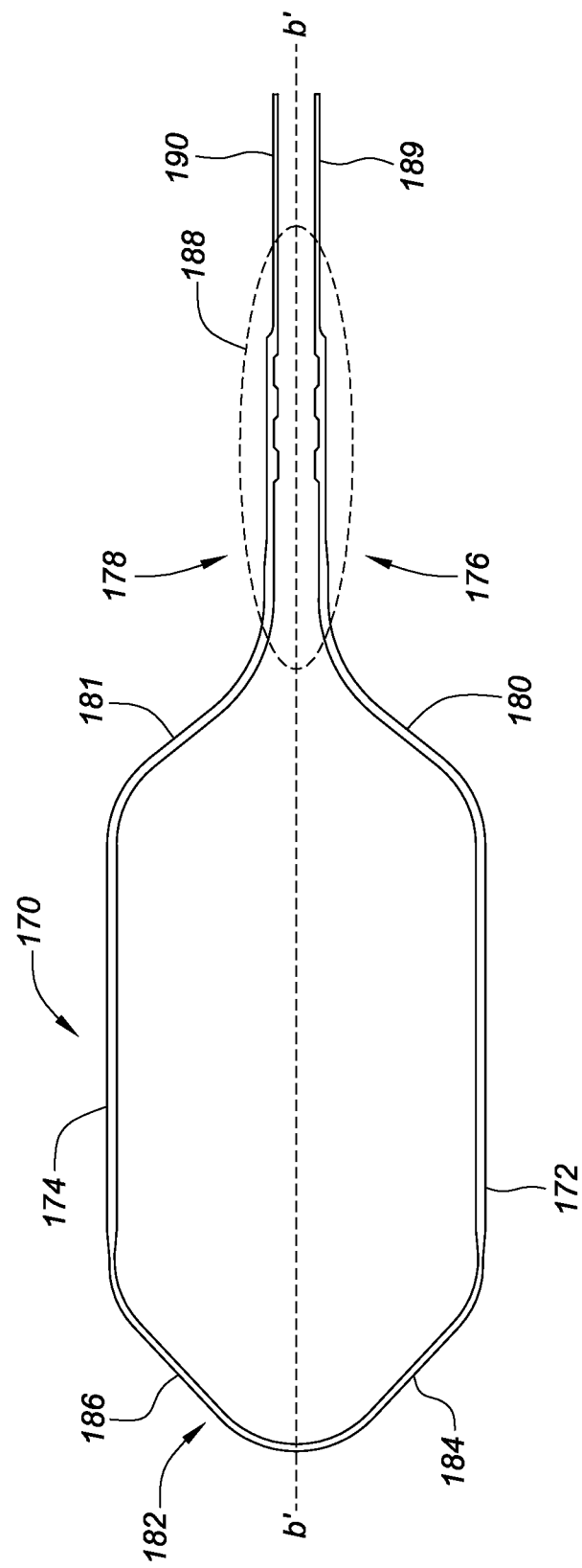
FIG. 3 is a top view of an outboard understructure of a high density electrode mapping catheter depicted in FIG. 1A, according to various embodiments of the present disclosure.

FIG. 3 is a top view of an outboard understructure 170 (also referred to herein as outer understructure) of a high density electrode mapping catheter in FIG. 1A, according to various embodiments of the present disclosure. In some embodiments, the outboard understructure 170 can be formed from a flexible or spring-like material such as Nitinol and/or a flexible substrate, as previously discussed with respect to the inboard understructure. The outboard understructure 170 can include a first outboard arm understructure 172 and a second outboard arm understructure 174. As depicted, the outboard understructure 170 can include a first proximal outboard mounting arm 176 and a second proximal outboard mounting arm 178. The proximal outboard mounting arms 176, 178 can be inserted into a distal end of the catheter 107 (FIG. 1A, 1B) and can be used to connect the flexible tip portion 110 (FIG. 1A, 1B) to the distal end of the catheter 107. In some embodiments, the proximal outboard mounting arms 176, 178 can be inserted through a torsional spacer, as discussed herein.

In some embodiments, the outboard understructure 170 can define a tip longitudinal axis, depicted by line b'b'. In some embodiments, the outboard understructure 170 can be formed from a continuous element that includes a first rectangular cross-section. For example, the outboard understructure 170 can include the first proximal outboard mounting arm 176 and second proximal outboard mounting arm 178, which can extend along the tip longitudinal axis. The outboard understructure 170 can include a first outboard arm understructure 172 that extends distally from the first proximal outboard mounting arm 176 and can include a second outboard arm understructure 174 that extends distally from the second proximal outboard mounting arm 178. In some embodiments, the first outboard arm understructure 172 and the second outboard arm understructure 174 can extend parallel to the tip longitudinal axis b'b' and to one another.

In some embodiments, a first outboard transition understructure portion 180 can be disposed between the first proximal outboard mounting arm 176 and the first outboard arm understructure 172. The first outboard transition understructure portion 180 can be laterally flared away from the tip longitudinal axis b'b'. Additionally, a second outboard transition understructure portion 181 can be disposed between the second proximal outboard mounting arm 178 and the second outboard arm understructure 174. The second outboard transition understructure portion 181 can be laterally flared away from the tip longitudinal axis b'b'. In an example, the first outboard transition understructure portion 180 and the second outboard transition understructure portion 181 can be flared away from one another.

In some embodiments, the outboard understructure 170 includes a head portion 182 that is connected to distal ends of the first and second outboard arm understructures 172, 174. In some embodiments, the head portion 182 can be formed from a first tapered element 184 and a second tapered element 186 that each extend distally toward the tip longitudinal axis b'b' and converge at the longitudinal axis b'b'. In an example, the outboard understructure 170 can be symmetrical along either side of the tip longitudinal axis b'b'.

In some embodiments, the proximal portion of the outboard frame understructure 170 can include the first proximal outboard mounting arm 176 and the second proximal outboard mounting arm 178. In an example, the proximal portion of the outboard frame understructure 170 can include an outboard frame lock portion 188.

In some embodiments, a distal end of the first proximal outboard mounting arm 176 and the second proximal outboard mounting arm 178 can be connected to a proximal end of the first outboard transition understructure portion 180 and the second outboard transition understructure portion 181, respectively. The first proximal outboard mounting arm 176 can have a reduced lateral width with respect to the first outboard transition understructure portion 180 and the second proximal outboard mounting arm 178 can have a reduced lateral width with respect to the second outboard transition understructure portion 181. In an example, the outboard transition understructure portions 180, 181 and the proximal outboard mounting arms 176, 178 can be tapered at an outboard tapered transition area between the two elements.

In some embodiments, a proximal end of the outboard frame lock portion 188 can be connected to a proximal outboard tail portion that includes a first proximal outboard tail 189 and a second proximal outboard tail 190. The first proximal outboard tail 189 can be connected to the first proximal outboard mounting arm 176 and the second proximal outboard tail 190 can be connected to the second proximal outboard mounting arm 178. In an example, the proximal outboard mounting arms 176, 178 and the proximal outboard tails 189, 190 can be tapered at a tapered outboard tail transition area between the two elements.

As previously discussed, each portion of the outboard frame understructure 170, including the proximal tails 189, 190, proximal outboard mounting arms 176, 178, outboard arm understructures 172, 174, and head portion 182 can be formed from a planar substrate. For example, the planar substrate can have a rectangular cross-section, which can be beneficial, as further described herein. However, use of the planar substrate can also result in the planar substrate having defined edges, as previously discussed. As depicted in FIG. 3, the outboard understructure 170 can be formed from a planar piece of material. In an example, the outboard understructure 170 can be formed from an understructure with a rectangular and/or square shaped cross-section. In some embodiments, the outboard understructure 170 can be a continuous element that is formed from a single unitary piece of material.

Figure 4:
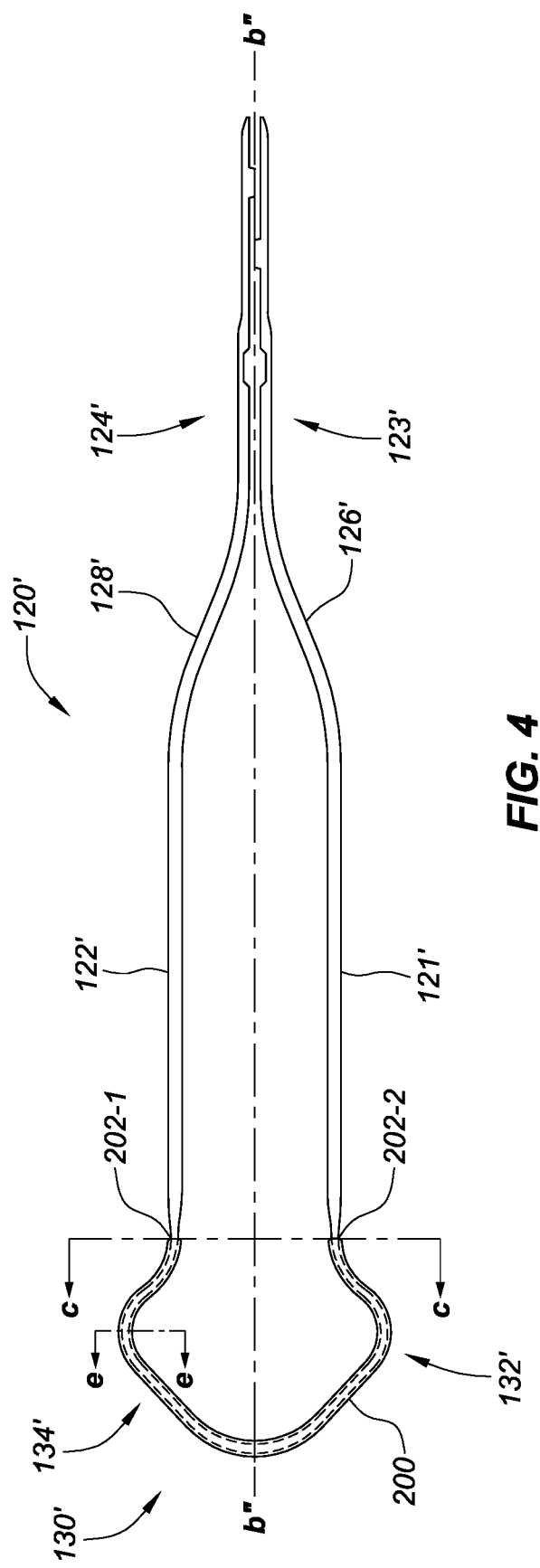
FIG. 4 is a top view of the inboard understructure depicted in FIGS. 2A and 2B with an intermediate inboard covering, according to various embodiments of the present disclosure.

FIG. 4 is a top view of the inboard understructure 120' depicted in FIGS. 2A and 2B with an intermediate inboard covering 200, according to various embodiments of the present disclosure. As previously discussed, the inboard understructure 120' can include a first inboard arm understructure 121' and a second inboard arm understructure 122' and a first proximal inboard mounting arm 123' and a second proximal inboard mounting arm 124', which can be inserted into a distal end of a catheter to secure the inboard understructure to the catheter. The first inboard arm understructure 121' can be connected to the first proximal inboard mounting arm 123' via a first transition understructure portion 126' and the second inboard arm understructure 122' can be connected to the second proximal inboard mounting arm 124' via a second transition understructure portion 128'.

The inboard understructure can include a flared head portion 130' that is connected to the distal ends of the first and second inboard arm understructures 121', 122'. The flared head portion 130' can include a first flared element 132' and a second flared element 134'. As previously discussed in relation to FIGS. 2A and 2B, as the first flared element 132 and the second flared element 134' extend distally, the elements 132', 134' can be laterally flared away from the tip longitudinal axis bb and away from one another, before extending toward the tip longitudinal axis bb" and toward one another.

In some embodiments, an intermediate inboard covering 200 can be disposed about the continuous element that forms the inboard understructure 120'. As previously discussed, the continuous element that forms the inboard understructure 120' can be formed from a planar substrate. In some embodiments, the planar substrate can have a rectangular cross-section that includes defined edges. The intermediate inboard covering 200 can be disposed about the continuous element, thus covering defined edges of the inboard understructure, as previously discussed. In some embodiments, the intermediate inboard covering 200 can be disposed about a portion of the continuous element that forms the flared head portion 130'. The flared head portion 130' can be defined as the distal end of the inboard understructure 120', which begins to laterally flare away from the tip longitudinal axis b"b". For example, the flared head portion 130' is depicted in FIG. 4 as including the portion of the inboard understructure 120' that is located to the left of (with respect to the page) the line cc (e.g., distally of line cc).

In some embodiments, the inboard understructure 120' may not include a flared head portion 130', however, the intermediate inboard covering 200 can still be disposed about a portion of the continuous element that forms the inboard understructure 120'. For example, the intermediate inboard covering 200 can be disposed over an entirety of the continuous element or can be partially disposed over a portion of the continuous element. In some embodiments, the intermediate inboard covering 200 can be disposed over the portion of the inboard understructure 120', which is not inserted in a distal end of a catheter. For example, the intermediate inboard covering 200 can be disposed over a portion of the inboard understructure 120' that is exposed and not located within the distal end of the catheter. In an example, the intermediate inboard covering can be disposed over the first transition understructure portion 126' and/or second transition understructure portion 128'. In some embodiments, the intermediate inboard covering can be disposed over the first transition understructure portion 126' and/or second transition understructure portion 128', as well as over portions of the inboard understructure 120' that are located distally to the first transition understructure portion 126' and/or second transition understructure portion 128'. In some embodiments, the intermediate inboard covering 200 can be disposed over the first inboard arm understructure 121' and second inboard arm understructure 122', as well as portions of the inboard understructure 120' that are distal to the first inboard arm understructure 121' and second inboard arm understructure 122'.

As further depicted with respect to FIG. 4, the intermediate inboard covering 200 can be disposed about the continuous element that forms the flared head portion 130'. In an example, the intermediate inboard covering 200 can be a tube that is slid over the flared head portion 130' or another portion of the inboard understructure 120'. For example, the tube can be slid over a proximal end of one of the first or second proximal inboard mounting arms 123', 124'. The tube can be cylindrical in shape, comprising a central lumen through which the continuous element that forms the inboard understructure 120' can pass. The tube can be slid along the continuous element until the tube is disposed along the portion of the continuous element that forms the flared head portion 130' or other portion of the inboard understructure 120'. The tube can be a heat shrink tube, in some embodiments. For example, the tube can be positioned along the portion of the continuous element that forms the flared head portion 130' and heat can be applied to the tube to shrink the tubing, to form the intermediate inboard covering 200. In some embodiments, the intermediate inboard covering 200 can be a coating that is applied to the continuous element that forms the flared head portion 130'. In an example, the coating can be applied via dipping the inboard understructure 120' into the coating and/or spraying the inboard understructure 120' with the coating.

In some embodiments, the intermediate inboard covering 200 can have two proximal ends 202-1, 202-2. As depicted, the two proximal ends 202-1, 202-2 are depicted as being positioned at the interface between the flared head portion 130' and the first and second inboard arm understructures 121', 122'. For example, the two proximal ends 202-1, 202-2 can be positioned where the first flared element 132' and the second flared element 134' begin to laterally flare away from the tip longitudinal axis b'''b'''. In some embodiments, and as depicted, the proximal ends 202-1, 202-2 are positioned at a same longitudinal position along the tip long longitudinal axis b'''b'''.

In some embodiments, the intermediate inboard covering 200 can include one layer of material (e.g., polymer, etc.) that covers a portion (e.g., flared head portion 130') of the first and/or second inboard arm understructures 121', 122'. However, in some embodiments, the intermediate inboard covering 200 can include more than one layer of material that covers the portion of the first and/or second inboard arm understructures 121', 122'. In an example, a first layer of material can cover the portion of the first and/or second inboard arm understructures 121', 122' and a second layer of material can be disposed over the first layer of material. For instance, a first layer of heat shrink material can be disposed over the portion of the first and/or second inboard arm understructures 121', 122' and a second layer of heat shrink material can be disposed over the first layer of heat shrink material.

The intermediate inboard covering 200 can serve the purpose of increasing a cross-sectional width of the continuous element and/or covering the defined edges of the planar substrate. For example, as further discussed herein, a defined edge that is covered by the intermediate inboard covering can become less defined, thus reducing an impact associated with the edge coming into contact with a tissue or other material.

Figure 5:
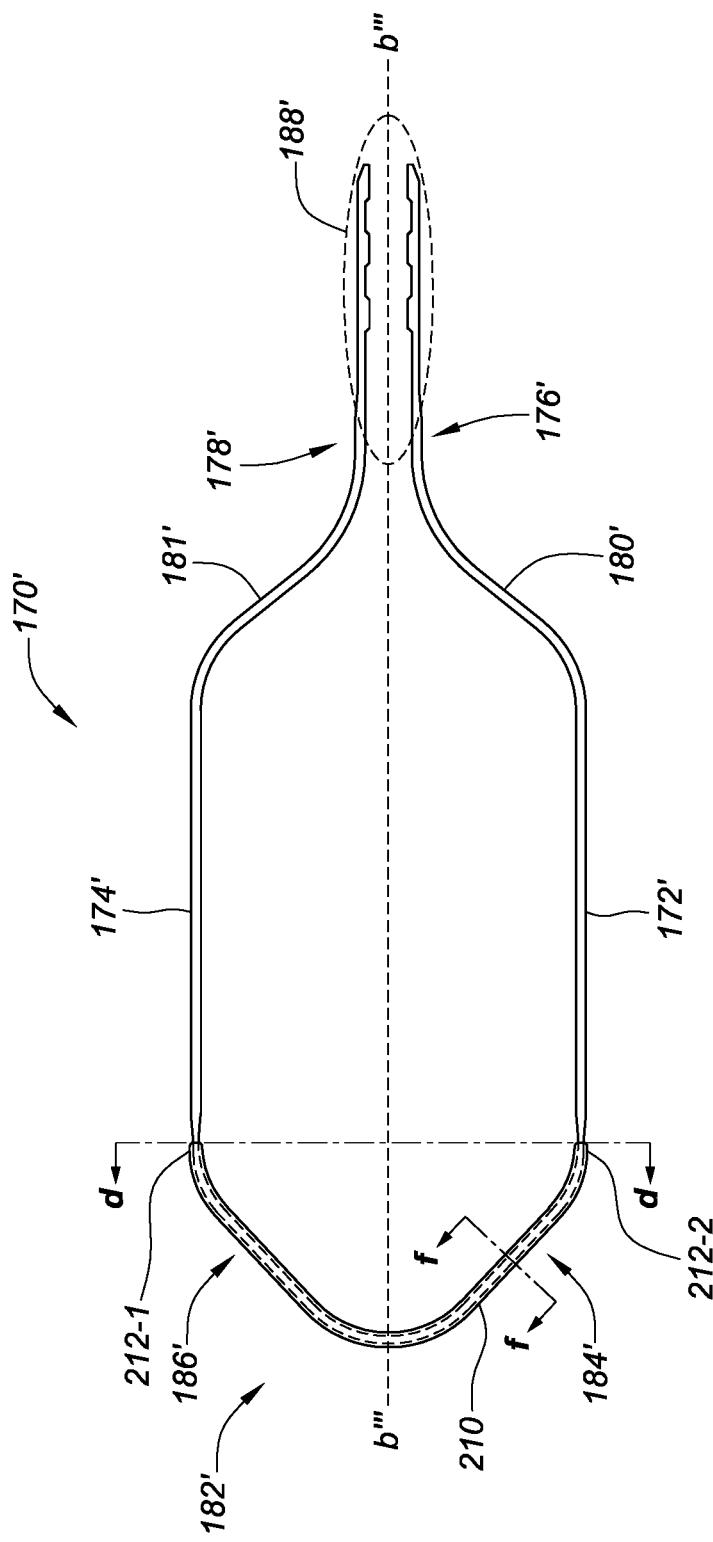
FIG. 5 is a top view of the outboard understructure depicted in FIG. 3 with an intermediate outboard covering, according to various embodiments of the present disclosure.

FIG. 5 is a top view of the outboard understructure depicted in FIG. 3 with an intermediate outboard covering, according to various embodiments of the present disclosure. As previously discussed, the outboard understructure 170' can include a first outboard arm understructure 172' and a second outboard arm understructure 174' and a first proximal outboard mounting arm 176' and a second proximal outboard mounting arm 178', which can be inserted into a distal end of a catheter to secure the inboard understructure to the catheter. The first outboard arm understructure 172' can be connected to the first proximal outboard mounting arm 176' via a first outboard transition understructure portion 180' and the second outboard arm understructure 174' can be connected to the second proximal outboard mounting arm 178' via a second outboard transition understructure portion 181'.

The outboard understructure 170 can include a head portion 182' that is connected to the distal ends of the first and second outboard arm understructures 172', 174'. The head portion 182' can include a first tapered element 184' and a second tapered element 186'. As previously discussed in relation to FIG. 3, as the tapered element 184' and the second tapered element 186' extend distally, the elements 184', 186' can each extend distally toward the tip longitudinal axis b'''b''' and converge at the longitudinal axis b'''b'''.

In some embodiments, an intermediate outboard covering 210 can be disposed about the continuous element that forms the outboard understructure 170'. As previously discussed, the continuous element that forms the outboard understructure 170' can be formed from a planar substrate. In some embodiments, the planar substrate can have a rectangular cross-section that includes defined edges. The intermediate outboard covering 210 can be disposed about the continuous element, thus covering defined edges of the inboard understructure, as previously discussed. In some embodiments, the intermediate outboard covering 210 can be disposed about a portion of the continuous element that forms the head portion 182'. The head portion 182' can be defined as the distal end of the outboard understructure 170', which begins to taper (e.g., converge) toward the tip longitudinal axis b'''b'''. For example, the head portion 182' is depicted in FIG. 5 as including the portion of the outboard understructure 170' that is located to the left of (with respect to the page) the line dd (e.g., distally of line dd).

In some embodiments, the intermediate outboard covering 210 can be disposed over an entirety of the continuous element that forms the outboard understructure 170' or can be partially disposed over a portion of the continuous element. In some embodiments, the intermediate outboard covering 210 can be disposed over the portion of the outboard understructure 170', which is not inserted in a distal end of a catheter. For example, the intermediate outboard covering 210 can be disposed over a portion of the outboard understructure 170' that is exposed and not located within the distal end of the catheter. In an example, the intermediate outboard covering can be disposed over the first proximal outboard mounting arm 176' and/or second proximal outboard mounting arm 178'. In some embodiments, the intermediate outboard covering can be disposed over the first proximal outboard mounting arm 176' and/or second proximal outboard mounting arm 178', as well as over portions of the outboard understructure 170' that are located distally to the first proximal outboard mounting arm 176' and/or second proximal outboard mounting arm 178'. In some embodiments, the intermediate outboard covering 210 can be disposed over the first outboard arm understructure 172' and second outboard arm understructure 174', as well as portions of the outboard understructure 170' that are distal to the first outboard arm understructure 172' and second outboard arm understructure 174'.

As further depicted with respect to FIG. 5, the intermediate outboard covering 210 can be disposed about the continuous element that forms the head portion 182'. In an example, the intermediate outboard covering 210 can be a tube that is slid over the head portion 182' or another portion of the outboard understructure 170'. For example, the tube can be slid over a proximal end of one of the first or second proximal outboard mounting arms 178', 176'. The tube can be cylindrical in shape, comprising a central lumen through which the continuous element that forms the outboard understructure 170' can pass. The tube can be slid along the continuous element that forms the outboard understructure 170' until the tube is disposed along the portion of the continuous element that forms the head portion 182' or other portion of the outboard understructure 170'. In some embodiments, the tube can be formed from a polymer (e.g., polytetrafluoroethylene (PTFE)). The tube can be a heat shrink tube, in some embodiments. For example, the tube can be positioned along the portion of the continuous element that forms the head portion 182' and heat can be applied to the tube to shrink the tubing, to form the intermediate outboard covering 210. In some embodiments, the intermediate outboard covering 210 can be a coating that is applied to the continuous element that forms the head portion 182'.

In some embodiments, the intermediate outboard covering 210 can have two proximal ends 212-1, 212-2. As depicted, the two proximal ends 212-1, 212-2 are depicted as being positioned at the interface between the head portion 182' and the first and second outboard understructures 172', 174'. For example, the two proximal ends 212-1, 212-2 can be positioned where the first tapered element 184' and the second tapered element 186' begin to taper toward the tip longitudinal axis b'''b'''. In some embodiments, and as depicted, the proximal ends 212-1, 212-2 are positioned at a same longitudinal position along the tip longitudinal axis b'''b'''.

The intermediate outboard covering 210 can serve the purpose of increasing a cross-sectional width of the continuous element and/or covering the defined edges of the planar substrate. For example, as further discussed herein, a defined edge that is covered by the intermediate outboard covering can become less defined, thus reducing an impact associated with the edge coming into contact with a tissue or other material.

Figure 6A:
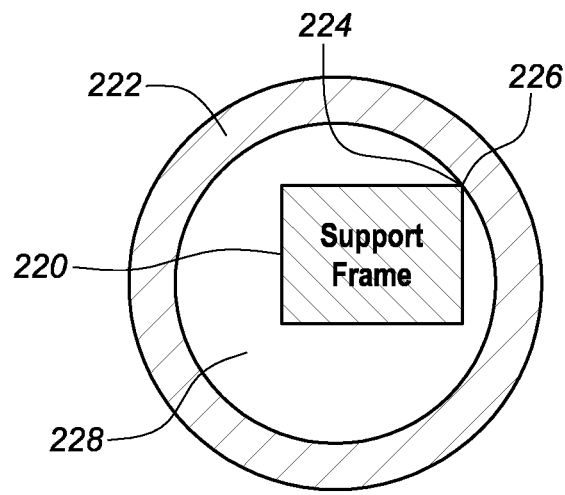
FIG. 6A is a cross-sectional view of an understructure and a covering disposed about a continuous element of the inboard understructure, according to various embodiments of the present disclosure.

FIG. 6A is a cross-sectional view of a covering disposed about a continuous element of an inboard understructure, according to various embodiments of the present disclosure. FIG. 6A depicts an inboard understructure 220, as previously discussed herein. As further depicted, and previously discussed, the inboard understructure 220 can have a rectangular cross-section, resulting in the inboard understructure 220 having defined edges (e.g., defined edge 224). In some embodiments, a covering 222 can be disposed about the inboard understructure 220. For example, the covering 222 can be disposed about a continuous element that forms the inboard understructure 220. The covering 222 can extend along a longitudinal axis and can define a covering lumen 228, in some embodiments, through which the continuous element that forms the inboard understructure 220 extends.

As previously discussed, the inboard understructure 220 can contact the covering 222, as a result of the inboard understructure 220 flexing from contact with tissue and/or deployment from a sheath, for example. The primary portion of the inboard understructure 220 that contacts the covering 220 can be the defined edges (e.g., defined edge 224). As a result of the contact between the inboard understructure 220 and particularly the defined edge 224 and the covering 222, holes can eventually be formed in the covering 222. In an example, contact between the inboard understructure 220 and the covering 222 can be concentrated in a contact area 226 where the defined edge 224 contacts the covering 222, causing a force exerted by the inboard understructure 220 to be concentrated on the covering 222 at the contact area 226. For ease of discussion, reference is made with regard to the inboard understructure 220, although embodiments discussed in relation to FIGS. 6A and 6B also apply to an outboard understructure.

Figure 6B:
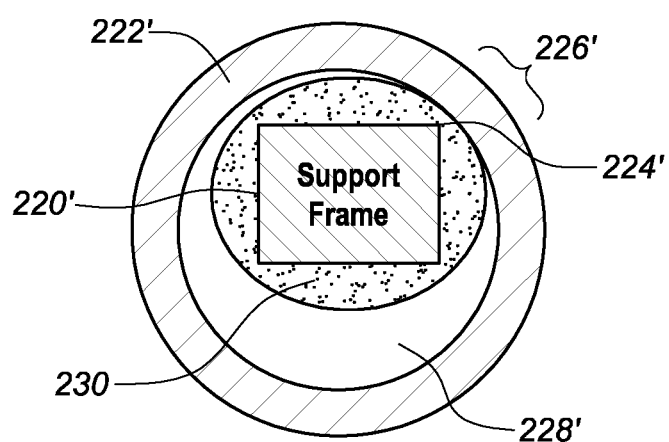
FIG. 6B is a cross-sectional view of an understructure and an intermediate inboard covering disposed about a first continuous element of the inboard understructure, along with a covering disposed about the understructure and the intermediate inboard covering, according to various embodiments of the present disclosure.

FIG. 6B is a cross-sectional view of an intermediate inboard covering 230 disposed about a first continuous element of the inboard understructure 220', along with a covering 222' disposed about the inboard understructure 220' and the intermediate inboard covering 230, according to various embodiments of the present disclosure. In some embodiments, as discussed herein, the intermediate inboard covering 230 can be disposed about the continuous element, thus covering defined edges of the inboard understructure 220', as previously discussed. Accordingly, contact between the inboard understructure 220' (e.g., defined edge 224') and the covering 222' can be concentrated in a contact area 226' where the portion of the intermediate inboard covering 230 that covers the defined edge 224' contacts the covering 222', causing a force exerted by the inboard understructure 220 to be concentrated on the covering 222 at the contact area 226'. In contrast to FIG. 6A, the contact area 226' has a greater surface area than the contact area 226 depicted in FIG. 6A. Accordingly, a force exerted by the inboard understructure 220' on the covering 222' can be reduced in relation to the force exerted by the inboard understructure 220, which does not include inboard covering 230, on the covering 222. Therefore, the amount of wear on the covering 222' caused by a defined edge 224' of the inboard understructure 220' can be reduced, as a result of the force exerted between the inboard understructure 220' and the inboard covering 222' being distributed across a greater surface area.

Figure 7A:
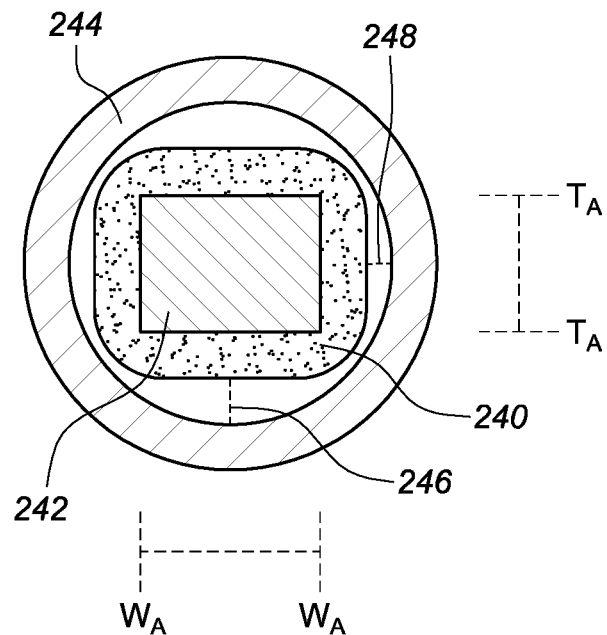
FIG. 7A is a cross-sectional view of an understructure and an intermediate covering of a first outer diameter disposed about a first continuous element of the understructure, along with a covering disposed about the understructure and the intermediate covering, according to various embodiments of the present disclosure.
Figure 7B:
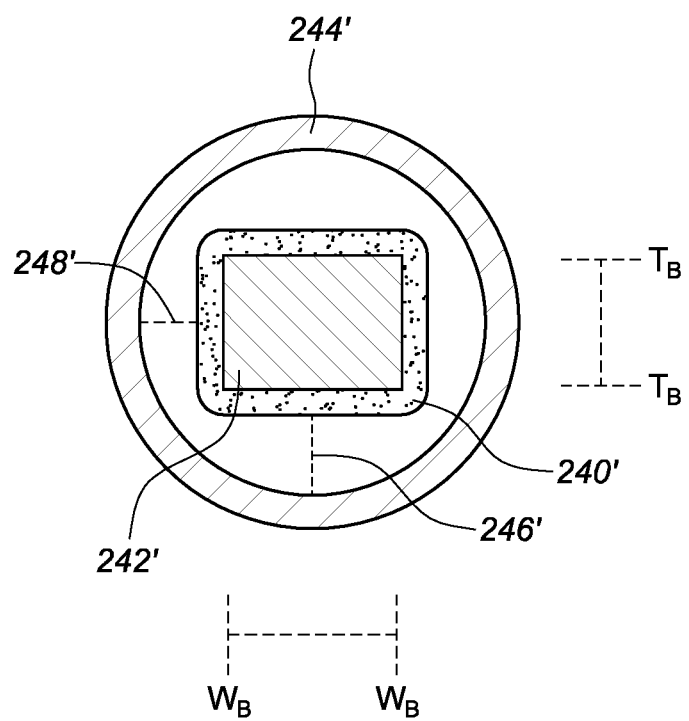
FIG. 7B is a cross-sectional view of an understructure and an intermediate covering of a second outer diameter disposed about a first continuous element of the understructure, along with a covering disposed about the understructure and the intermediate covering, according to various embodiments of the present disclosure.
Figure 7C:
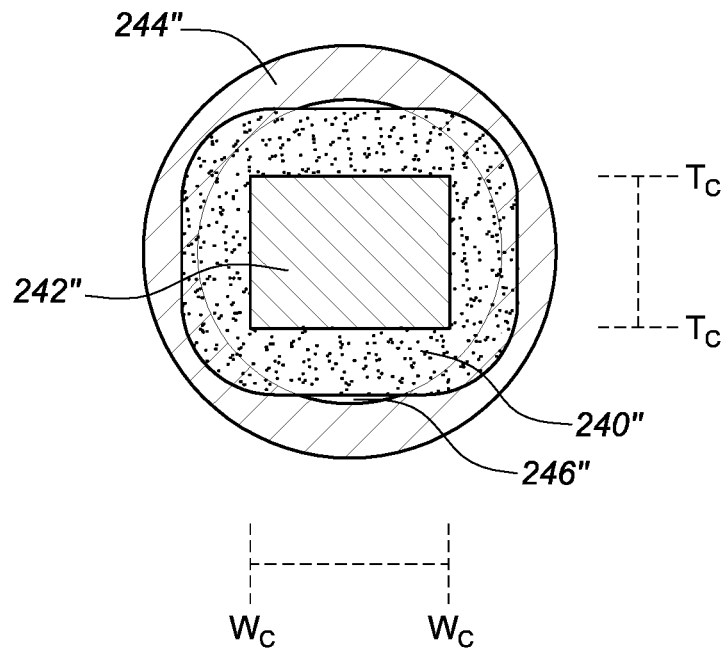
FIG. 7C is a cross-sectional view of an understructure and an intermediate covering of a third outer diameter disposed about a first continuous element of the understructure, along with a covering disposed about the understructure and the intermediate covering, according to various embodiments of the present disclosure.

FIG. 7A is a cross-sectional view of an intermediate covering 240 disposed about a first continuous element of an understructure 242, along with a covering 244 disposed about the understructure 242 and the intermediate inboard covering 240, according to various embodiments of the present disclosure. FIGS. 7A to 7C can depict a cross-sectional view of an understructure, such as those depicted in relation to FIGS. 4 and 5, along lines ee and ff. With further reference to FIG. 7A, the understructure 242 can be an inboard and/or outboard understructure, as discussed herein. In some embodiments, the intermediate covering 240 can be disposed around the understructure 242. For example, the intermediate covering 240 can be a heat shrink tube, in some embodiments, which is disposed around the intermediate covering 240. The understructure 242 can be slid through a lumen of the heat shrink tube until the heat shrink tube is properly positioned. In some embodiments, heat can be applied to the heat shrink tube to shrink the tube around the understructure 242. In some embodiments, the intermediate covering 240 can also be a coating applied to the understructure 242, as further discussed herein. In some embodiments, as depicted in FIG. 7A, the covering 244 can be disposed around the intermediate covering 240 and the understructure 242. In some embodiments, as depicted in FIGS. 7A to 7C, the covering 244 can have an inner diameter in a range from 0.013 inches to 0.015 inches, although the covering can have an inner diameter that can be less than or greater than the defined range. As depicted in FIG. 7A, the covering 244 can have an inner diameter of 0.014 inches. In some embodiments, as depicted in FIGS. 7A to 7C, the intermediate covering 240 can have a wall thickness in a range from 0.001 inches to 0.003 inches, although the wall thickness of the intermediate covering 240 can be less than or greater than the defined range. As depicted in FIG. 7A, the intermediate covering 240 can have a wall thickness of 0.002 inches. In some embodiments, as depicted in FIGS. 7A to 7C, the understructure 242 can have a width, defined by line $W_A W_A$, in a range from 0.0075 to 0.0085 inches, although the width of the understructure 242 can be less than or greater than the defined range. As depicted in FIG. 7A, the understructure 242 can have a width of 0.008 inches. In some embodiments, as depicted in FIGS. 7A to 7C, the understructure 242 can have a thickness, defined by line $T_A T_A$, in a range from 0.0055 to 0.0065 inches, although the thickness of the understructure 242 can be less than or greater than the defined range. As depicted in FIG. 7A, the understructure 242 can have a thickness of 0.006 inches.

FIGS. 7A to 7C depict varying sizes of gaps between an exterior surface of the intermediate covering 240 and an interior wall of the covering 244. With reference to FIG. 7A, in some embodiments, a bottom gap 246 between the exterior bottom/top surface of the intermediate covering 240 and the interior wall of the covering 244 can be in a range from 0 to 0.004 inches, although the gap can be of a smaller or larger size than the range provided. As depicted in FIG. 7A, the bottom gap 246 can be 0.003 inches. In some embodiments, a side gap 248 between the exterior surface of the intermediate covering 240 and the interior wall of the covering 244 can be in a range from 0 to 0.004 inches, although the gap can be of a smaller or larger size than the range provided. As depicted in FIG. 7A, the side gap 248 can be 0.002 inches. In some embodiments, an interference fit can exist between the exterior surface of the intermediate covering 240 and the interior surface of the covering 244, as further discussed in relation to FIG. 7C.

FIG. 7B is a cross-sectional view of an understructure 242' and an intermediate covering 240' disposed about a first continuous element of the understructure 242', along with a covering 244' disposed about the understructure 242' and the intermediate covering 240', according to various embodiments of the present disclosure. The understructure 242' can be an inboard and/or outboard understructure, as discussed herein. In some embodiments, the intermediate covering 240' can be disposed around the understructure 242'. In some embodiments, the intermediate covering 240' can also be a tube and/or coating applied to the understructure 242'. In some embodiments, as depicted in FIG. 7B, the covering 244' can be disposed around the intermediate covering 240' and the understructure 242'. As depicted in FIG. 7B, the covering 244' can have an inner diameter of 0.015 inches. As depicted in FIG. 7B, the intermediate covering 240' can have a wall thickness of 0.001 inches. As depicted in FIG. 7B, the understructure 242' can have a width, defined by line $W_B W_B$, of 0.0075 inches. As further depicted in FIG. 7C, the understructure 242' can have a thickness, defined by line $T_B T_B$, of 0.0055 inches. As depicted in FIG. 7B, a bottom gap 246' can be 0.004 inches. As depicted in FIG. 7B, the side gap 248' can be 0.003 inches.

FIG. 7C is a cross-sectional view of an understructure 242" and an intermediate covering 240" disposed about a first continuous element of the understructure 242", along with a covering 244" disposed about the understructure 242" and the intermediate covering 240", according to various embodiments of the present disclosure. The understructure 242" can be an inboard and/or outboard understructure, as discussed herein. In some embodiments, the intermediate covering 240" can be disposed around the understructure 242". In some embodiments, the intermediate covering 240" can also be a tube and/or coating applied to the understructure 242". In some embodiments, as depicted in FIG. 7C, the covering 244" can be disposed around the intermediate covering 240" and the understructure 242". As depicted in FIG. 7C, the covering 244" can have an inner diameter of 0.013 inches. As depicted in FIG. 7C, the intermediate covering 240" can have a wall thickness of 0.003 inches. As depicted in FIG. 7c, the understructure 242" can have a width, defined by line $W_C W_C$, of 0.0085 inches. As further depicted in FIG. 7C, the understructure 242" can have a thickness, defined by line $T_C T_C$, of 0.0065 inches.

As depicted in FIG. 7C, the bottom gap 246" can be 0 inches. In some embodiments, an interference fit can exist between the exterior surface of the intermediate covering 240" and the interior surface of the covering 244", as further discussed in relation to FIG. 7C. For example, as depicted, an interference fit can exist between a side of the exterior surface of the intermediate covering 240" and an interior side surface of the covering 244". For example, a width of the intermediate covering 240" can exceed a width of an inner diameter of the covering 244". Accordingly, the covering 244" can be stretched over the intermediate covering 240".

In some embodiments, as depicted in FIGS. 7A to 7C, the intermediate covering 240 can reduce a size of the gap between the understructure 242 and the inner wall of the covering 244. In some embodiments, the reduction in the size of the gap between the understructure 242 and the inner wall of the covering 244 can reduce the possible stretching/thinning of the covering 240. For example, as a high density mapping catheter that includes the understructure 242 is folded as the catheter is passed through a sheath, there can be friction between the sheath and the outer covering 244, which can pull against the outer covering. By introducing a smaller gap between the understructure 242 and the interior surface of the covering 244 via the intermediate covering 240, there can be a reduction in the amount of friction between the covering 244 and surfaces through which the catheter is being passed (e.g., surfaces of a sheath). Additionally, an amount by which the covering 244 is necked down (e.g., radially collapsed inward) is reduced. Thus, wear associated with the covering 244 can be reduced.

Figure 7D:
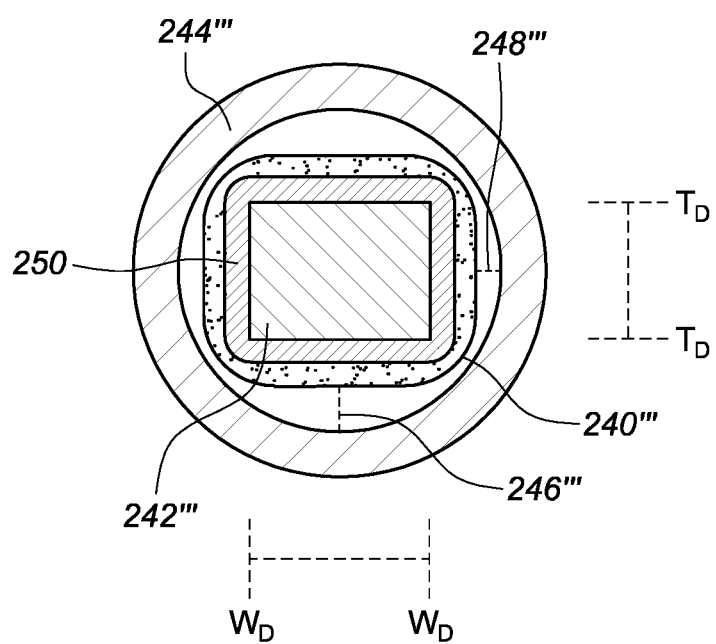
FIG. 7D is a cross-sectional view of an understructure and an inner first intermediate covering and outer second intermediate covering of the first outer diameter depicted in FIG. 7A, disposed about a first continuous element of the understructure, according to various embodiments of the present disclosure.

FIG. 7D is a cross-sectional view of an understructure 242''' and an inner first intermediate covering 250 and outer second intermediate covering 240''' of the first outer diameter depicted in FIG. 7A, disposed about a first continuous element of the understructure 242''', according to various embodiments of the present disclosure. As depicted in FIG. 7D, an inner first intermediate covering 250 can be disposed about the understructure 242''' and an outer second intermediate covering 240''' can be disposed about the inner first intermediate covering 250 to create first and second layers of covering 250, 240''', as previously discussed herein. With reference to FIG. 7D, in some embodiments, a bottom gap 246''' between the exterior bottom/top surface of the outer second intermediate covering 240''' and the interior wall of the covering 244''' can be in a range from 0 to 0.004 inches, although the gap can be of a smaller or larger size than the range provided. As depicted in FIG. 7D, the bottom gap 246''' can be 0.003 inches, although the gap can be smaller or larger in size. For example, the gap can be in the range as that discussed in relation to FIGS. 7B and 7C. In some embodiments, a side gap 248''' between the exterior surface of the outer second intermediate covering 240''' and the interior wall of the covering 244''' can be in a range from 0 to 0.004 inches. As depicted in FIG. 7A, the side gap 248''' can be 0.002 inches, although the gap can be of smaller or larger size. For example, the gap can be in the range as that discussed in relation to FIGS. 7B and 7C.

In some embodiments, as previously discussed, an intermediate covering can consist of more than one layer of material that is disposed about the understructure 242". In an example, the inner first intermediate covering 250 of material can cover the understructure 242''' and an outer second intermediate covering 240''' can be disposed over the first layer of material. For instance, a first layer of heat shrink material can be disposed over a portion of the understructure 242''' and a second layer of heat shrink material can be disposed over the first layer of heat shrink material. In some embodiments, by including more than one layer of material that covers the portion of the understructure 242", a greater diameter can be achieved, reducing an amount by which a covering 244''' is necked down.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for a layered high density electrode mapping catheter has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A flexible catheter tip, comprising:
   an inboard understructure that defines a tip longitudinal axis, wherein the inboard understructure is formed from a first continuous element that includes a first rectangular cross-section;
   an intermediate inboard covering disposed about the first continuous element that forms a distal portion of the inboard understructure;
   an inboard covering disposed about the first continuous element and the intermediate inboard covering;
   an outboard understructure that extends along the tip longitudinal axis, wherein the outboard understructure is formed from a second continuous element that includes a second rectangular cross-section;
   an intermediate outboard covering disposed about the second continuous element that forms a distal portion of the outboard understructure; and
   an outboard covering disposed about the first continuous element and the intermediate outboard covering, wherein the intermediate inboard and outboard coverings and the inboard and outboard coverings are non-conductive coverings, and wherein each of the intermediate inboard and outboard coverings and the inboard and outboard coverings extend about a respective circumference of a respective one of the inboard understructure and the outboard understructure.

2. The flexible catheter tip of claim 1, wherein the intermediate inboard covering is disposed between the inboard understructure and the inboard covering.

3. The flexible catheter tip of claim 1, wherein the inboard covering is disposed about a majority of the first continuous element.

4. The flexible catheter tip of claim 1, wherein the intermediate outboard covering is disposed between the outboard understructure and the outboard covering.

5. The flexible catheter tip of claim 1, wherein the intermediate inboard covering and the intermediate outboard covering are formed from a heat shrink material.

6. The flexible catheter tip of claim 1, wherein the inboard understructure includes:
   a first proximal inboard mounting arm and second proximal inboard mounting arm that extend along the tip longitudinal axis;
   a first inboard arm understructure that extends distally from the first proximal inboard mounting arm;
   a second inboard arm understructure that extends distally from the second proximal inboard mounting arm; and
   a flared head portion connected to distal ends of the first and second inboard arm understructures.

7. The flexible catheter tip of claim 1, wherein the intermediate inboard covering comprises an inner intermediate inboard covering disposed about the first continuous element and an outer intermediate inboard covering disposed about the inner intermediate inboard covering.

8. A flexible catheter tip, comprising:
   a flexible understructure that defines a tip longitudinal axis, wherein the flexible understructure is formed from a first continuous element that includes a first rectangular cross-section;
   an intermediate covering disposed about the first continuous element;
   a covering disposed over the intermediate covering, such that the intermediate covering is disposed between the covering and the flexible understructure, wherein the intermediate covering and the covering are non-conductive coverings and extend about a circumference of the flexible understructure.

9. The flexible catheter tip of claim 8, further comprising a gap between the intermediate covering and the covering.

10. The flexible catheter tip of claim 8, wherein an interference fit exists between the intermediate covering and the covering.

11. The flexible catheter tip of claim 8, further comprising a gap between the intermediate covering and the covering, wherein a size of the gap is in a range from 0 inches to 0.004 inches.

12. The flexible catheter tip of claim 8, wherein the intermediate covering and the covering are formed from one or more polymers.

13. The flexible catheter tip of claim 8, wherein the intermediate covering is formed from more than one layer of material.

14. The flexible catheter tip of claim 13, wherein the more than one layer of material includes a heat shrink material.

15. A flexible catheter tip, comprising:
an inboard understructure that defines a tip longitudinal axis, wherein the inboard understructure is formed from a first continuous element that includes a first rectangular cross-section, the first continuous element defining first and second inboard arm understructures and a flared head portion connected to a distal end of each of the first and second inboard arm understructures;
an intermediate inboard covering disposed about the flared head portion;
an outboard understructure that extends along the tip longitudinal axis, wherein the outboard understructure is formed from a second continuous element that includes a second rectangular cross-section, the second continuous element defining first and second outboard arm understructures and a head portion connected to a distal end of each of the first and second outboard arm understructures;
an intermediate outboard covering disposed about the second continuous element that forms the head portion;
an inboard covering disposed about the intermediate inboard covering and the flared head portion; and
an outboard covering disposed about the intermediate outboard covering and the head portion, wherein the intermediate inboard and outboard coverings and the inboard and outboard coverings are non-conductive coverings and each of the intermediate inboard and outboard coverings and the inboard and outboard coverings extend about a respective circumference of a respective on of the inboard understructure and the outboard understructure.

16. The flexible catheter tip of claim 15, wherein:
the intermediate inboard covering includes a first proximal end and a second proximal end; and
the first proximal end and the second proximal end being positioned at an interface between the flared head portion and the first and second inboard arm understructures.

17. The flexible catheter tip of claim 16, wherein:
the intermediate outboard covering includes a first proximal end and a second proximal end; and
the first proximal end and the second proximal end being positioned at an interface between the head portion and the first and second outboard arm understructures.

18. The flexible catheter tip of claim 15, further comprising an electrode disposed on the outboard covering.

* * * * *